(12) United States Patent
Lasner et al.

(10) Patent No.: US 10,765,413 B2
(45) Date of Patent: Sep. 8, 2020

(54) HANDLE FOR MICROSURGICAL INSTRUMENTS

(71) Applicants: Jeffrey I Lasner, Purchase, NY (US); Michael E Lasner, Mt Kisco, NY (US)

(72) Inventors: Jeffrey I Lasner, Purchase, NY (US); Michael E Lasner, Mt Kisco, NY (US)

( * ) Notice: Subject to any disclaimer, the term of this patent is extended or adjusted under 35 U.S.C. 154(b) by 269 days.

(21) Appl. No.: 15/829,505

(22) Filed: Dec. 1, 2017

(65) Prior Publication Data

US 2018/0153535 A1 Jun. 7, 2018

Related U.S. Application Data

(60) Provisional application No. 62/497,795, filed on Dec. 21, 2016.

(51) Int. Cl.
| | |
|---|---|
| *A61B 17/00* | (2006.01) |
| *A61B 17/06* | (2006.01) |
| *A61B 17/062* | (2006.01) |
| *A61B 17/30* | (2006.01) |
| *A61B 17/29* | (2006.01) |
| *A61B 17/28* | (2006.01) |

(52) U.S. Cl.
CPC ...... *A61B 17/00234* (2013.01); *A61B 17/062* (2013.01); *A61B 17/06061* (2013.01); *A61B 17/30* (2013.01); *A61B 17/2833* (2013.01); *A61B 2017/00429* (2013.01); *A61B 2017/2845* (2013.01); *A61B 2017/2946* (2013.01); *A61B 2017/305* (2013.01)

(58) Field of Classification Search
CPC ........ A61B 17/00234; A61B 17/06061; A61B 17/062; A61B 17/30; A61B 17/2833; A61B 2017/00429; A61B 2017/2845; A61B 2017/2946; A61B 2017/305; A61B 17/2841; A61B 17/2909; B29C 45/00; B25G 1/02; B25G 1/102; Y10T 16/476; B29L 2031/753
USPC .................................... 606/1; 30/28; 16/430
See application file for complete search history.

(56) References Cited

U.S. PATENT DOCUMENTS

| | | | |
|---|---|---|---|
| 2006/0009795 A1* | 1/2006 | Lasner ................... | A61B 17/30 606/174 |
| 2013/0247333 A1* | 9/2013 | Bender et al. ........... | B25G 1/00 16/430 |

* cited by examiner

*Primary Examiner* — Erin M Piateski
(74) *Attorney, Agent, or Firm* — Joseph M Fowler

(57) ABSTRACT

A surgical instrument made from flexibly resilient sheet metal has a handle formed into a sheet metal beam having a convex shape for improved strength. Raised uninterrupted arcuate protrusions on the outer surface of the handle of the instrument are provided to add additional strength and to provide improved grip retention when the surgical instrument is being used during surgical procedures. The improved handle is shown integrally as part of a needle holder capable of clamping surgical needles of varying diameters.

10 Claims, 5 Drawing Sheets

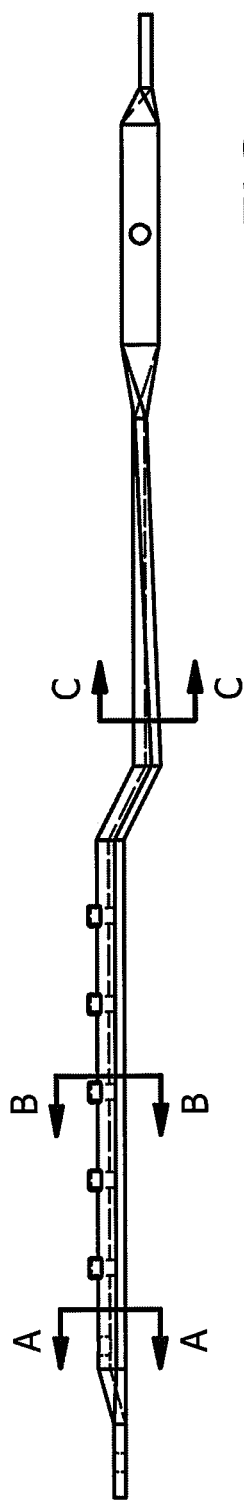
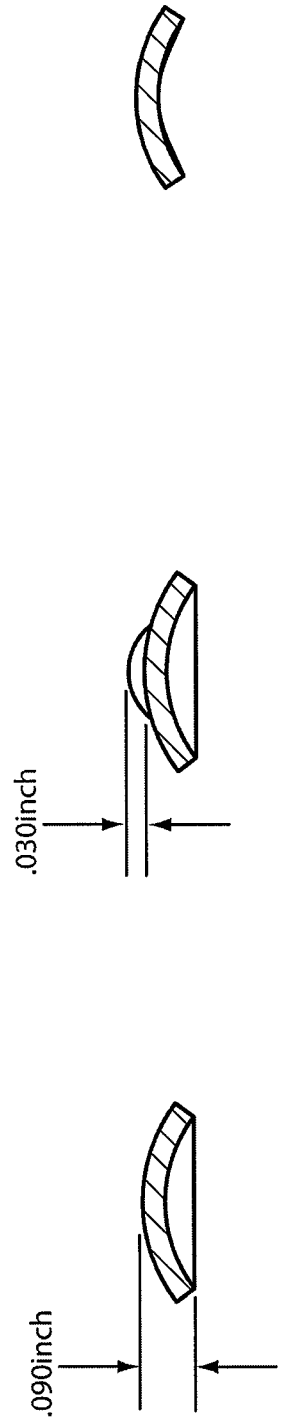
FIG. 5
SECTION C-C
SCALE 3 : 1
FIG. 7
SECTION B-B
SCALE 3 : 1
FIG. 8
.030inch
SECTION A-A
SCALE 3 : 1
FIG. 6
.090inch

HANDLE FOR MICROSURGICAL INSTRUMENTS

CROSS-REFERENCE TO RELATED APPLICATIONS

The present application claims the benefit of U.S. Provisional Application No. 62/497,795, filed on Dec. 2, 2016 which is expressly incorporated in its entirety by reference herein.

FIELD OF THE INVENTION

The present invention relates to microsurgical instruments that can be used in all aspects of surgery as needle holders, scissors, forceps and other devices.

BACKGROUND OF THE INVENTION

The use of sheet metal handles made from flexibly resilient, medical grade material has been pioneered by the present inventors beginning notably with U.S. Pat. No. 4,527,331 which addressed the problem of how to create a low cost, high quality scissors that opened automatically after closure. This development was followed by U.S. Pat. No. 6,592,603 which incorporated interlocking springs joining the ends of each pair of handles which significantly reduced the pressure needed to close the paired handles. The reduced force needed to close the handles enabled use of this design for development of several different manually-operated surgical instruments. Thereafter, U.S. Pat. No. 7,497,867 B2 taught mechanical changes which improved the stiffness and beam strength needed to achieve the desired resultant closing forces of the instruments. Surgical instruments that had stiffer and lower profiles broadened the applicability for this flexibly resilient sheet metal design, especially when the instruments were being used in tightly confined spaces frequently encountered during common surgical procedures.

U.S. Pat. No. 7,497,867 B2 taught use of the inventive handles as part of the design for manually adjustable scissors and forceps. However, needle holders using this design, while satisfactory for suturing mucosa or blood vessels, were inadequate at maintaining a secure hold on larger needles when pushed into denser tissue. The comparatively greater compressive force required to penetrate heavier and denser tissue results in undesirable flexion in weaker parts of the instrument which introduces instability during the suturing procedure. Furthermore, smooth surfaces on the outside of the sheet metal handles make them more prone to slip in the gloved hands of the surgeon when large manual forces are applied especially when the instrument handles become slippery in an environment prone to become wet. There exists, therefore, a current need for further improvements in flexible sheet metal handles for surgical instruments.

It is of course a requirement that a surgeon be able to maintain a firm, positive grip on an instrument during manual surgical procedures. Instabilities introduced by undesirable flexion or slippage of the tool must be avoided or mitigated. Many conventional surgical instruments—unlike the relatively flexible sheet metal instruments of the present invention—are machined from thicker, solid materials. These instruments are much heavier and less comfortable for the surgeon to use over long periods which results in greater strain and tiredness of the fingers, hands and arms. To make these heavier instruments easier to grip, cross-hatched knurling is often machined onto the outer surfaces of the handles. Instruments of the present design are not easily knurled as they are made from relatively thin, flat sheet materials. Knurling—a low height marking procedure—is not particularly effective when the surgical instrument being manipulated is lightweight which is one of the primary benefits of the sheet metal band design.

Another significant disadvantage of more conventional surgical instruments made from thicker solid materials—needle holders in particular—is that they are prone to permanent deformation if a needle too large in diameter is clamped in the jaws of the instrument, a not uncommon occurrence. Surgical needles generally have round cross sections and are not designed to be diametrically deformable. When a needle just slightly too large in diameter is forcibly clamped by the surgeon clinician using a conventional needle holder, the elastic limit associated with the jaw material of the scissor-like device is often exceeded permanently deforming the instrument by splaying the jaws out of tolerance. Therefore, an object of the present invention is to provide a sheet metal needle holder strong enough to resist excessive bending of the handle and yet flexibly springy and resilient enough to allow the jaw portion of a needle holder to accept a variety of different diameter needles without destroying the instrument.

An approach to one of the foregoing problems, taught by Bender in publication US20130247333 A1, describes the addition of protrusions extending radially outward from the sheet metal handle of a needle holder along its longitudinal axis. The idea is that the protrusions increase frictional engagement with the clinician surgeon's fingers compared to the more slippery condition presented by a smooth surface.

The instruments shown in the Bender application are known as Castroviejo and Barraquer microsurgical instruments. The needle holder, in particular, is intended to be used by a clinician who will hold or grip the instrument between thumb and fingers and delicately roll a suture into place rather than employing a much larger movement such as a wrist or elbow rotation. As a consequence, the Bender publication describes a largely unsatisfactory solution for two important reasons, first, Bender's protrusions are stamped or formed from sheet metal material in a manner that interrupts the integrity of the beam which further weakens the strength of the handle while gripping the needle. And second, the humps or protrusions on Bender's handle are constructed using a design that places the edges of the protrusions parallel or co-axial with the longitudinal axis of the instrument. This feature runs counter to proper or best practice use of the instrument as the side edges of the protrusions have a tendency to snag the gloves of the clinician thereby inhibiting the rolling thumb and finger motion employed by the clinician during performance of a delicate procedure.

An important feature of surgical instruments made from flexibly resilient sheet metal is that they are both flexible and resilient in the sense that they resist permanent deformation much more readily than surgical instruments made from solid cast materials or surgical instruments machined from wire or bar stock. But the flexibility is also a limitation in some cases as sheet metal will yield more readily to bending moments depending upon the location of forces acting upon the structure.

Therefore, to overcome the limitations of the prior art, the primary object of the invention is to provide an improved handle design that can deliver the required compression forces where necessary—resisting deformation—and, at the same time, remain consonant with best practice use of an instrument which will allow a surgeon to maintain tactile sensitivity while keeping a firm and positive hold on an instrument that is gripped using only finger pressure.

Another object of the present invention, and, specifically an object of the inventive handle integrally formed into an embodiment as a needle holder, is the design of an instrument capable of gripping needles of different diameters without permanent damage to the needle holder.

BRIEF SUMMARY OF THE INVENTION

A handle having a curved convex profile is provided for a surgical instrument in which a plurality of curved or arcuate protrusions are placed orthogonally with respect to the central longitudinal axis of a surgical instrument. The curved or arcuate protrusions project radially from the outside surface of the handle and are placed in an uninterrupted line. The protrusions have smooth outer surfaces so as not to catch, snag or negatively impinge on adjacent surfaces which may be present such as gloves worn by a clinician during a surgical procedure. The curved or arcuate shape of the protrusions, by nature of their shape and placement, are adapted to increase frictional finger pressure during use thereby preventing inadvertent slippage of the instrument. The raised protrusions contribute greater mechanical stiffness to the formed sheet metal beams which comprise each handle of a dual handle instrument such as a needle holder or forceps. The coupled sheet metal beams of the inventive handle are adapted to withstand without flexing the maximum pressure normally exerted between the thumb and fingers of the hand of a surgical clinician in the performance of suturing or clamping.

On the forward end of the instrument distal from the inventive handle part is the working end of a surgical needle holder. Jaws of the needle holder are supported by flexibly resilient sheet metal parts which can accept a variety of needles of different diameters due to the springiness or inherent resilience of the sheet material.

Various other features, objects and advantages of the present invention will become apparent from the following description taken with reference to the accompanying drawings.

BRIEF DESCRIPTION OF THE DRAWINGS

FIG. 5 is a side view of the sheet metal part shown in FIG. 4.

FIG. 6 is an enlarged view in cross section taken along the lines A_A of the sheet metal part shown in FIG. 5.

FIG. 7 is an enlarged view in cross section taken along the lines B_B of the sheet metal part shown in FIG. 5.

FIG. 8 is an enlarged view in cross section taken along the lines C_C depicting the curved or arcuate protrusions in the handle portion of the sheet metal part shown in FIG. 5.

DETAILED DESCRIPTION OF THE INVENTION

Figure 1:
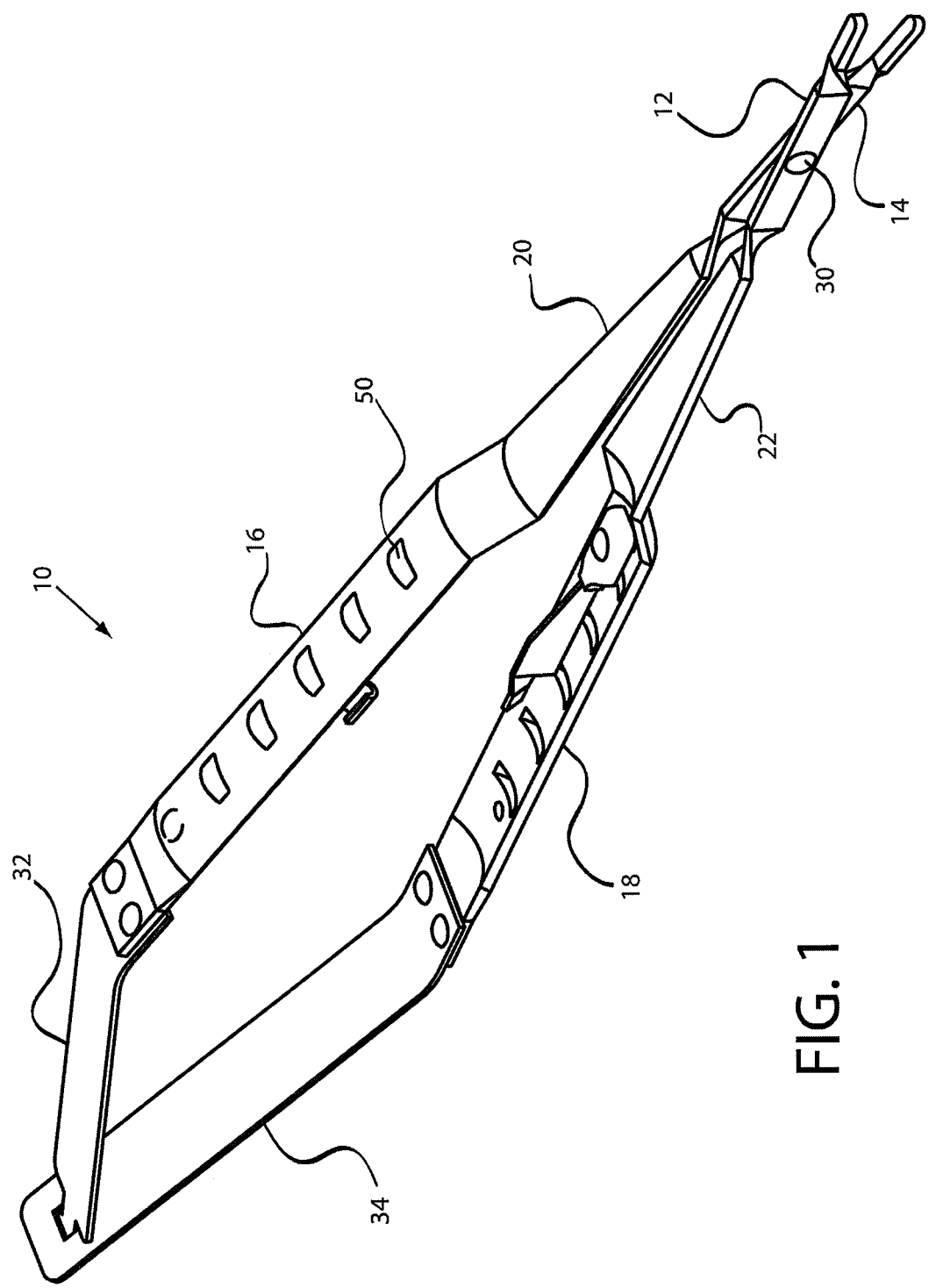
FIG. 1 is a perspective view of a Barraquer style needle holder instrument incorporating the inventive handle.

FIG. 1 of the drawings is a depiction of a surgical instrument assembly 10 commonly used for holding needles for suturing tissue. Although instrument 10 in this embodiment is a needle holder, it should be regarded as only representative of the kind of instruments which can use the inventive handle. Instruments using this handle may include scissors, forceps and other manually operable devices that are generally suitable for use in a surgical operatory. The handle portions of instrument 10 are referred to generally by numerals 18 and 16.

Figure 2:
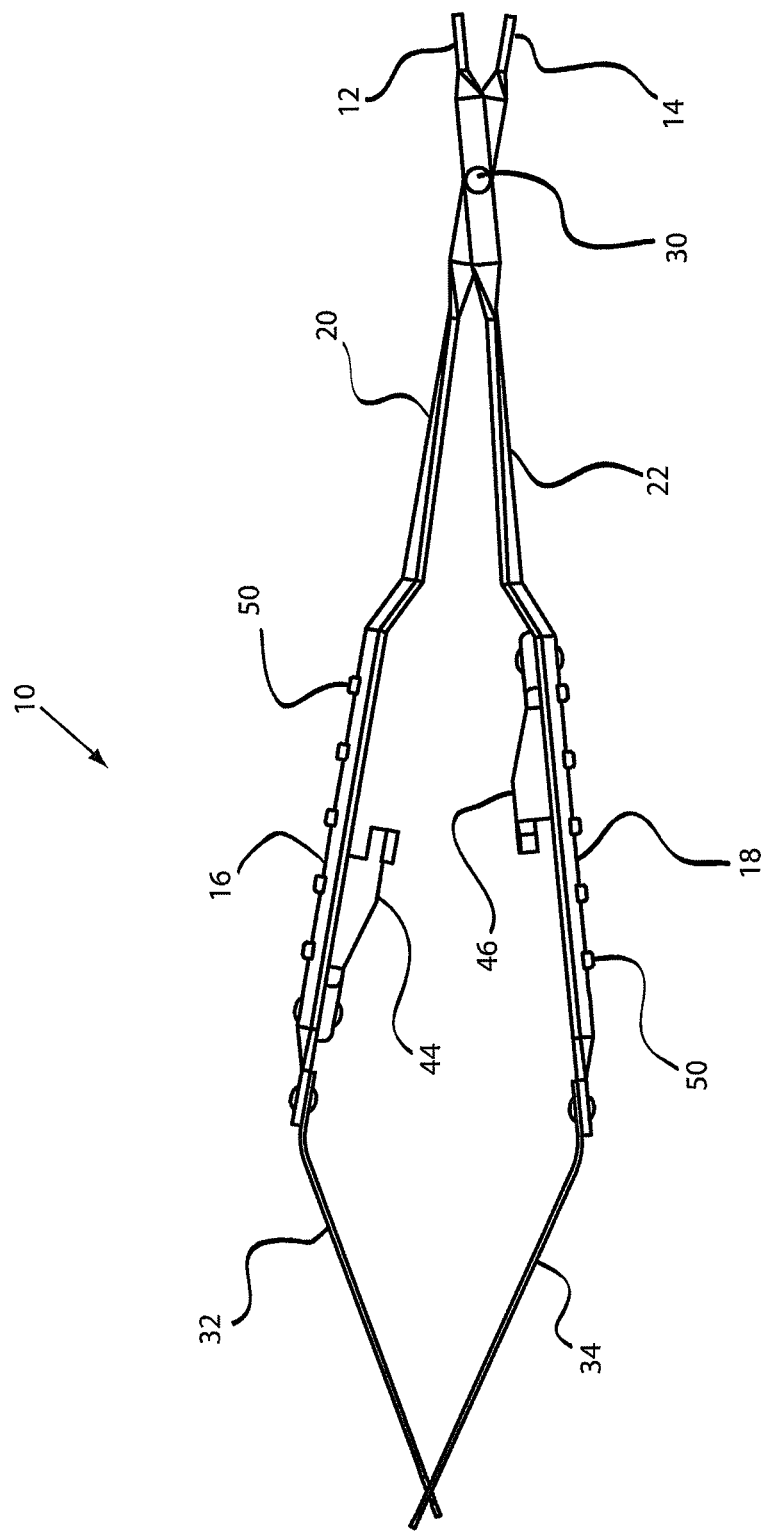
FIG. 2 is a side view of the instrument in FIG. 1 in an open position.

FIG. 1 is a perspective view showing instrument 10 in an open position. In FIG. 2, instrument 10 is shown in a closed position.

As depicted in FIG. 1, needle holder 10 comprises a pair of clamp parts 12 and 14 extending longitudinally to shank portions 22 and 20 respectively. Shank portions 22 and 20 extend to and are integral with handle portions 18 and 16 respectively. The clamp parts 12 and 14 are connected to one another pivotally by mechanical fastener 30 effectively forming a clampable jaw as the clamp parts 12 and 14 overlap one another when oriented as shown. Movement of handles 18 and 16 toward each other causes the clamp jaws to close and movement of handles 18 and 16 away from each other cause the clamp jaws to open.

Figure 3:
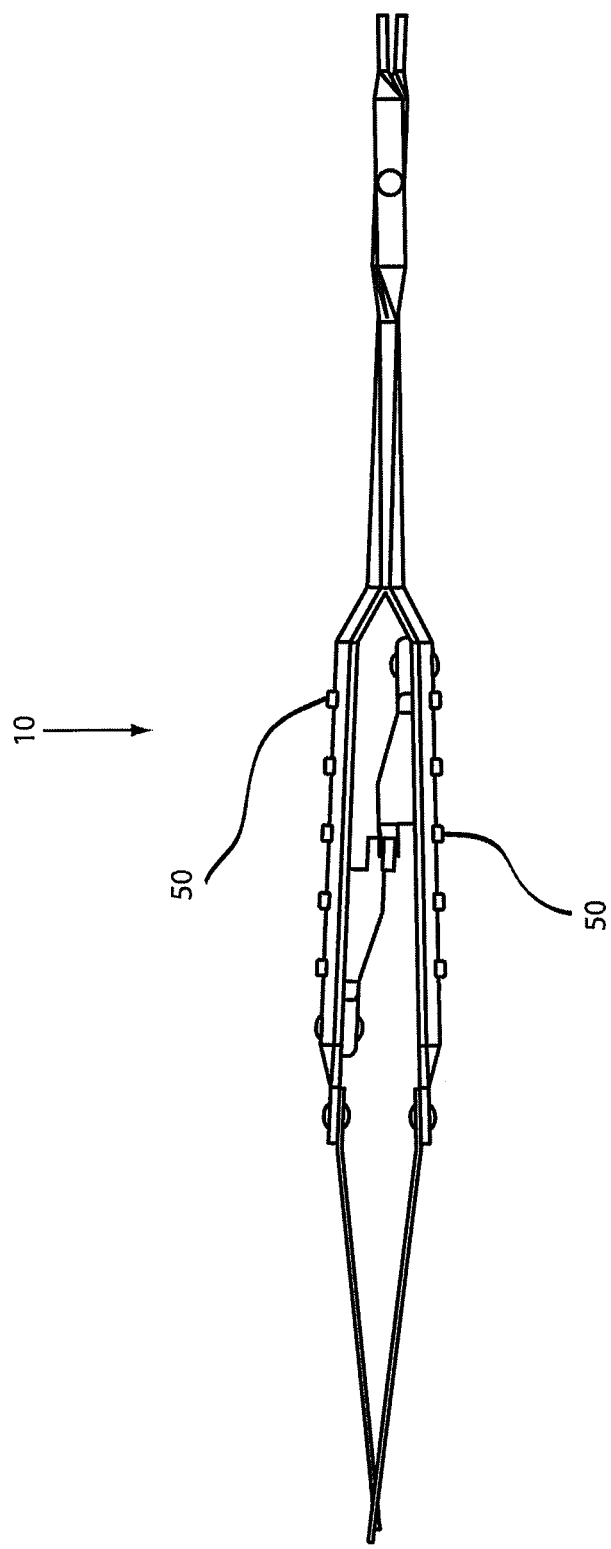
FIG. 3 is a side view of the instrument in FIG. 1 in a closed or locked position.

Opposing spring-biased engagement mechanisms 44 and 46 in FIG. 2 fastened to the underside of each handle 18 and 16 are adapted to mutually engage mechanically into a closed or locked condition as shown in FIG. 3.

Leaf springs, 32 and 34, located at one end of each handle, 16 and 18, provide biasing means to keep the handles separated. The leaf springs 32,34 are interlocked at the end opposite their individual attachments to each handle as depicted in FIGS. 1 and 2. At the discretion of the surgeon clinician, the opposing handles are pressed toward one another bringing the spring-biased locking mechanisms 44 and 46 close enough to physically connect and remain engaged. The surgical clinician can selectively disengage the mechanism by subsequent pressure on handles 18 and 16 allowing the needle holder 10 to return to the open, pre-engaged condition depicted in FIG. 1.

When the present embodiment of the invention is in use as part of needle holder 10, the clinician surgeon grips the handles between fingers and thumb. The clinician presses both handles of the needle holder to firmly capture the needle and directs the needle insertion by gingerly rotating the instrument using only the thumb and fingers. The raised protrusions 50 located on the outer surface of the handles 18 and 16 allow the clinician to keep a firm grip on the holder by pressing the surfaces of the protrusions into his or her finger tips.

Figure 4:
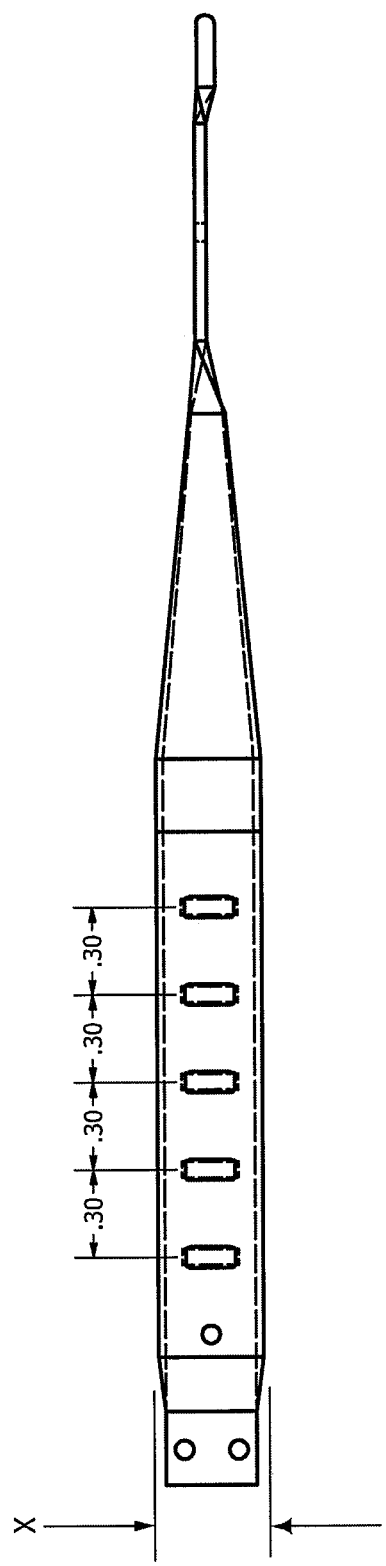
FIG. 4 is a top view of part of a needle holder fabricated integrally with the inventive handle of the microsurgical instrument depicted in FIG. 1.

As shown in the FIGS., and especially in FIG. 1 and FIG. 4, the raised protrusions 50 are shown evenly spaced along the longitudinal axis of the handle. The edges and surfaces of the raised, arcuate protrusions 50 have smooth surfaces and slightly radiused edges to avoid tearing and entanglement with surgical gloves.

The sheet metal component part shown in FIG. 4 is normally fabricated from medical grade stainless steel or stainless spring steel although other materials having similar mechanical characteristics suitable for medical use in surgical procedures may be utilized. The component part in FIGS. 4 and 5 comprises one half of the needle holder embodiment without the leaf springs 32,34, fasteners, and interlocking components 44,46. Overall, the component part is approximately 130 mm (5") long, 9 mm wide (0.355") and 1.1 mm (0.043") in thickness. The raised arcuate protrusions 50 are each approximately 0.77 mm (0.03") high spaced approximately 7.65 mm (0.30") apart. Each protrusion 50 is located on the apex of the external surface of the convex handle portion of the component part and each is positioned orthogonally with respect to the longitudinal axis. The protrusions 50 are centered across approximately 45% of the top surface width of the convex shape of the sheet metal handle. Each of the five protrusions 50 shown in FIG. 4 extends approximately 1.8 mm (0.07") in the longitudinal direction of the component part.

The increased beam strength of each of the handle parts is a function of the composition of the component material and the convex shape imparted to the material with the additional arcuate shape imposed on top of the outer surface of the beam. FIG. 6 is a cross section view of the convex shape in the distal direction of the component part shown in FIG. 5. FIG. 7 is a cross section view of the convex shape in the forward end of the component in the direction of the clamp jaw in this embodiment. FIG. 8 is a cross section view in the mid-handle portion of the component part shown in FIG. 5 depicting the raised arcuate shape visible across the convex width of the component part.

While the invention has been specifically described in connection with the preferred embodiments illustrated in the drawings, it is understood that these Figures are for illustration and not limitation and that modifications are possible without departing from the scope of the invention as described and presently disclosed, therefore, it is intended that all suitable modifications and equivalents be understood to fall within the true spirit of the invention and the scope of the claims appended here.

What is claimed:

1. A handle for a surgical instrument, comprising, a pair of flexibly resilient sheet metal beams, each formed into a convex shape, having a plurality of arcuate protrusions projecting outward from the convex surface of said beams, said convex shape extending the full length of the longitudinal axis of each handle with said protrusions placed orthogonally with respect to a central longitudinal axis of the surgical instrument, said arcuate protrusions located on the apex of the convex shapes extending across about 45% of the convex surface width of each of said beams, said protrusions emerging from but not fully penetrating the material thickness of the convex beams.

2. The handle for the surgical instrument as described in claim 1 in which said protrusions have smooth outer surfaces so as not to catch, snag or negatively impinge upon adjacent surfaces.

3. The handle for the surgical instrument as described in claim 2 in which said protrusions, by nature of their shape and placement, are adapted to increase frictional finger pressure during use thereby preventing slippage of said instrument during a surgical procedure.

4. The handle for the surgical instrument as described in claim 3 in which said protrusions are raised arcuate shapes across the convex width of the handle which impart increased beam strength and contribute greater mechanical stiffness to the handle.

5. The handle for the surgical instrument as described in claim 4 in which the flexibly resilient sheet metal is medical grade stainless steel.

6. A handle for a surgical instrument integrally connected to a pair of clamp parts made from flexibly resilient sheet metal, each clamp part extending longitudinally to a shank portion which extends to and is integral with a handle portion;

each handle portion is formed into a beam of convex shape having a plurality of raised arcuate protrusions projecting outward from the convex surface of said beam, said protrusions placed orthogonally with respect to a central longitudinal axis of the handle portion, said arcuate protrusions located on the apex of the convex shape extending across about 45% of the convex surface width of said beam, said protrusions emerging from but not fully penetrating the material thickness of said convex beam;

said clamp parts are pivotally connected by a mechanical fastener forming a clampable jaw which closes or opens responsive to pivotal movement of the handle portions toward and away from each other;

said clampable jaw capable of holding a range of suturing needles of different diameters without incurring permanent deformation.

7. The handle for the surgical instrument as described in claim 6 in which interlocking leaf springs, fastened to one end of each handle portion, provide biasing means to keep the handles separated.

8. The handle for the surgical instrument as described in claim 6 in which the flexibly resilient sheet metal is medical grade stainless steel.

9. A handle for a surgical instrument integrally connected to a pair of clamp parts made from flexibly resilient sheet metal, each clamp part extending longitudinally to a shank portion which extends to and is integral with a handle portion;

each handle portion is formed into a beam of convex shape 130 mm long (5") about 9 mm (0.355") wide and 1.1 mm (0.043") in thickness having a plurality of raised arcuate protrusions each about 0.77 mm (0.03") high, spaced about 7.65 mm (0.30") apart, each protrusion extending about 1.8 mm (0.07") in the longitudinal direction of the handle portion, projecting outward from the convex surface of said beam, said protrusions placed orthogonally with respect to a central longitudinal axis of the handle portion, said arcuate protrusions located on the apex of the convex shape extending across about 45% of the convex surface width of said beam, said protrusions emerging from but not fully penetrating the material thickness of said convex beam;

said clamp parts are pivotally connected by a mechanical fastener forming a clampable jaw which closes or opens responsive to pivotal movement of the handle portions toward and away from each other;

said clampable jaw capable of holding a range of suturing needles of different diameters without incurring permanent deformation.

10. The handle for the surgical instrument as described in claim 9 in which interlocking leaf springs, fastened to one end of each handle portion, provide biasing means to keep the handles separated.

* * * * *